US00PP19615P3

(12) United States Plant Patent
Kellerhals et al.

(10) Patent No.: US PP19,615 P3
(45) Date of Patent: Jan. 6, 2009

(54) APPLE TREE NAMED 'MILWA'

(50) Latin Name: *Malus pumila*
Varietal Denomination: Milwa

(75) Inventors: Markus Kellerhals, Wädenswil (CH); Alfred Aeppli, Jegenstorf (CH)

(73) Assignee: Agroscope Changins-Wädenswil, Wädenswil (CH)

( * ) Notice: Subject to any disclaimer, the term of this patent is extended or adjusted under 35 U.S.C. 154(b) by 0 days.

(21) Appl. No.: 11/796,294

(22) Filed: Apr. 26, 2007

(65) Prior Publication Data

US 2008/0271214 P1 Oct. 30, 2008

(51) Int. Cl.
*A01H 5/00* (2006.01)

(52) U.S. Cl. ..... Plt./161

(58) Field of Classification Search ..... Plt./161
See application file for complete search history.

*Primary Examiner*—Annette H Para
(74) *Attorney, Agent, or Firm*—Stratton Ballew PLLC

(57) ABSTRACT

A new apple tree named 'Milwa' is disclosed. The fruit of the new variety is particularly notable for its eating quality and distinctive appearance. The fruit is firm, crunchy, juicy and fully flavored, and takes on a distinctive luminous red coloration as it ripens on the tree. 'Milwa' apples maintain favorable texture and firmness during and after long term storage.

2 Drawing Sheets

Latin name: *Malus pumila* Mill.
Variety denomination: 'Milwa'.

BACKGROUND OF THE VARIETY

'Milwa' is a new and distinct cultivar of apple tree *Malus pumila* Mill. This new cultivar is a product of a controlled breeding program carried out by the inventor at the Federal Research Station Agroscope Changins-Wädenswil at W ädenswil, Switzerland. 'Milwa' was one of several seedlings resulting from a cross made in 1982 of female parent XII A 277 ('Idared'×'Maigold') (not patented) and male parent 'Elstar' (not patented). A single tree of 'Milwa' on 'M27' rootstock was planted at Wädenswil, Switzerland in 1985, and was asexually propagated for further testing in 1988. 'Milwa' has been observed to remain true to type over successive asexually propagated generations.

BRIEF DESCRIPTION OF THE VARIETY

'Milwa' was selected for its suitability as a commercial apple tree variety. Fruit of 'Milwa' is notable for its globose shape and luminous red color. The characteristics that distinguish 'Milwa' from its parent and from other related varieties are set forth in Table 1.

TABLE 1

Comparison of 'Milwa' to Parents and Other Known Varieties (measurements given approximate)

| Variety | Fruit Shape | Skin Color | Tree Vigour | Harvest Date |
|---|---|---|---|---|
| Milwa | Globose conical | Orange red 34A to red purple 59A | Weak to medium | 1 week before Golden Delicious |
| Elstar | globose | Orange red 34C | vigorous | 2 weeks before Golden Delicious |
| Idared | Broad globose | Red 54A | medium | 1 week after Golden Delicious |

BRIEF DESCRIPTION OF THE PHOTOGRAPHS

DETAILED BOTANICAL DESCRIPTION OF THE VARIETY

Figure 1:
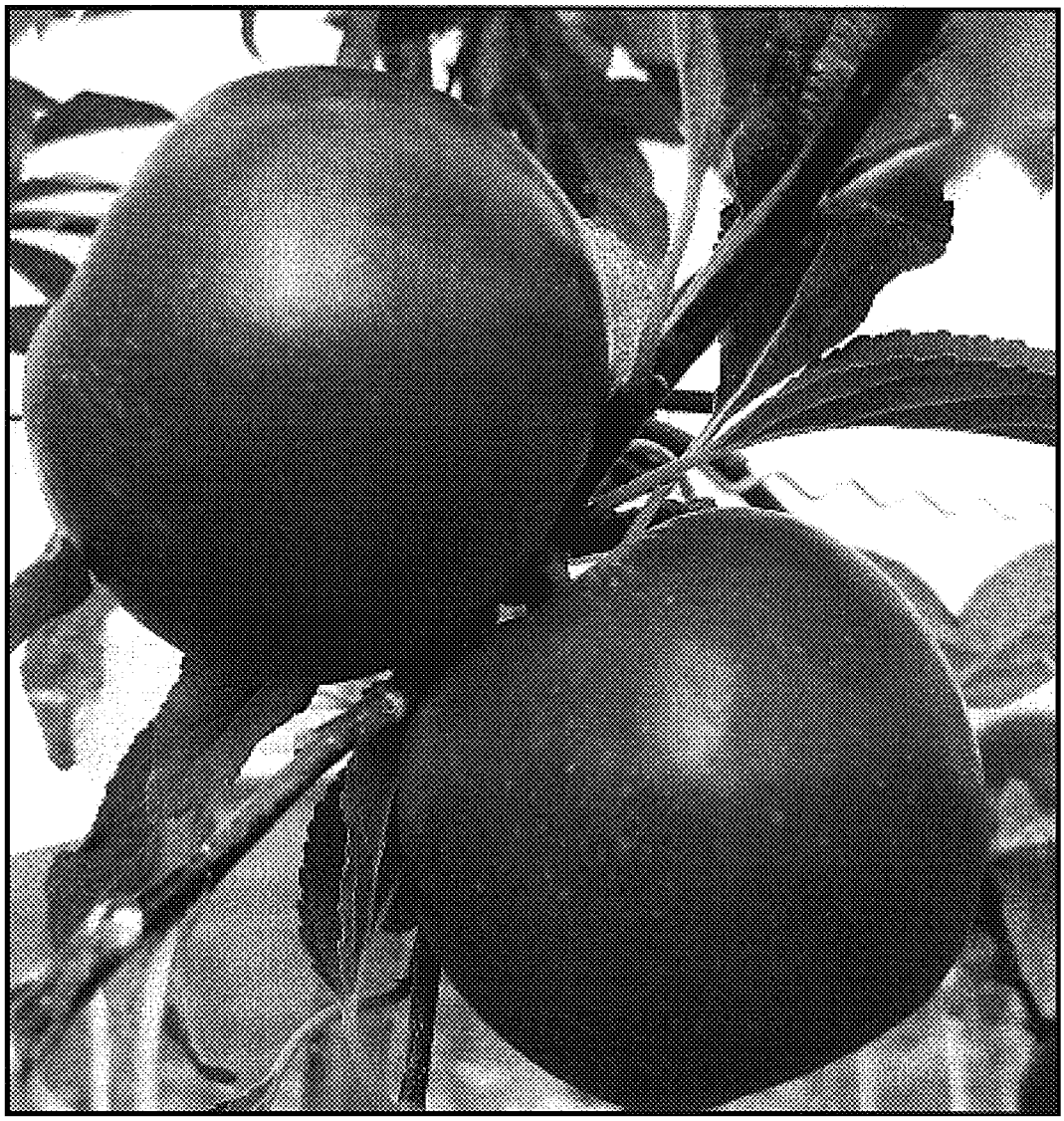
FIG. 1 shows the fruit and leaves of 'Milwa'.
Figure 2:
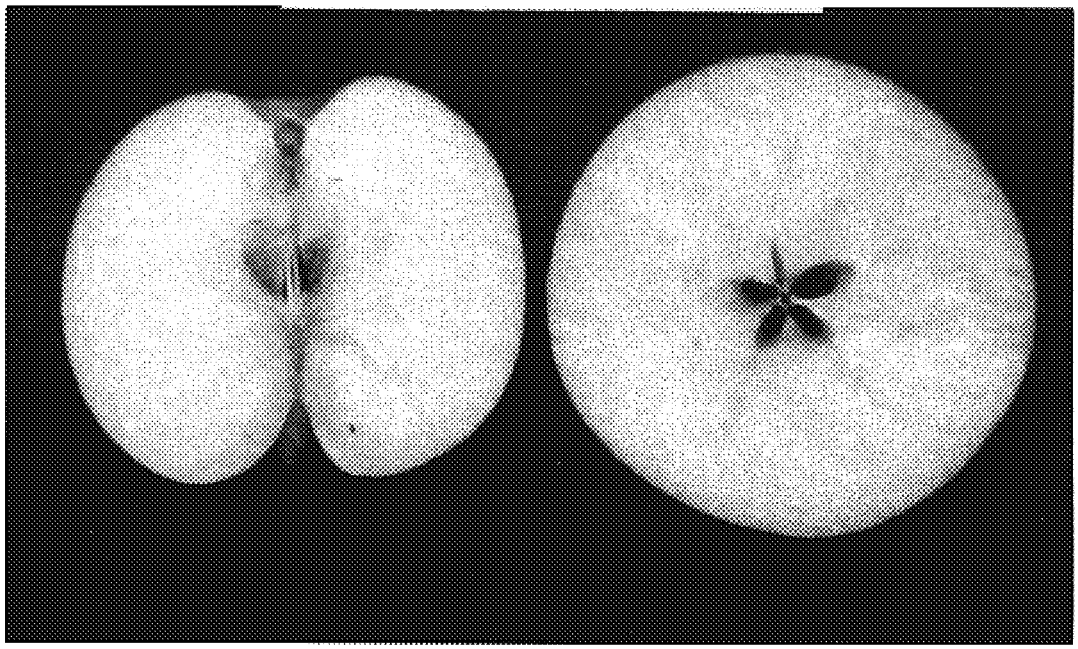
FIG. 2 shows longitudinal and transverse cross sections of 'Milwa' after storage.

The following detailed botanical description is based on observations made during the 2006 growing season at W ädenswil, Switzerland, of two year old trees grown an M9 rootstock in high density plantings. All colors are described according to The Royal Horticultural Society Colour Chart. It should be understood that the characteristics described will vary somewhat depending upon cultural practices and climatic conditions, and will vary with location and season. Quantified measurements are expressed as an average of measurements taken from a number of individual plants of the new variety. The measurements of any individual plant, or any group of plants, of the new variety may vary from the stated average.

Tree: Vigor — weak to medium (weaker than 'Golden Delicious'); Type — ramified; Habit — spreading; Height — medium high (2.30 m); Trunk diameter (at 30 cm above the graft union) — medium (31 mm); Bark texture — smooth to medium; Bark coloration — grey 201B; Lenticels — medium, oval, light yellow brown 158D.

Branch (fruiting branches located at around 1 m above the graft union): Length — long (avg. 62 cm); Diameter — medium-large (avg. 14.7 mm); Crotch angle — 70° to 90° (avg. 80°); Bark color — brown 200C; Lenticels — medium, oval, light yellow brown 158D.

One year old shoot: Length — short to medium (avg. 22 cm); Color — brown N200B; Pubescence (on upper half of the shoot) — medium strong; Thickness — medium (avg. 50 mm); Internode length — medium (avg. 14 mm);

Pubescence — medium-strong; Number of lenticels — very few (3 lenticels per $cm^2$).

Pollination: Diploid; Good pollinators include 'Braeburn,' 'Golden Delicious,' 'Iduna,' 'Pinova,' and 'Fuji'; No incompatibility with common pollinators has been observed.

Flower buds: Quantity per spur — 2 to 3; Shape — conical; Length — medium (avg. 10 mm); Diameter — medium (avg. 10 mm); Color — Red purple 61A.

Flowers: Color (flower buds) — Red Purple 60A; Diameter of open flower — very large; Relative position of petal margin — overlapping; Number per cluster — 5 to 7; Date of first bloom — April 8 in Loire Valley, France (4 days prior to Gala); Date of full bloom — April 11 in Loire Valley, France (4 days prior to Gala).

Petals: Number per flower — 5; Shape — oval; Length — long (avg. 22 mm); Width — wide (avg. 15 mm); Apex — round; Base — pointed; Margin — smooth to medium; Coloration of upper surface — purple 76A; Coloration of lower surface — purple 77D.

Pistils: Size — long (12 mm); Color — yellow green 145D.

Anthers: Quantity — numerous (avg. 18 per flower); Size — medium (avg. 2 mm); Presence of pollen — present; Color of pollen — yellow 4C.

Stigma: Size — small-medium (avg. 0.5 mm); Color — pale yellow 9C.

Style: Size — medium-long (avg. 9 mm); Color — yellow green N144D.

Ovary: Size — medium (avg. 1.8 mm); Color-green 134B.

Pedicel: Length — medium (avg. 18 mm); Diameter — thin (avg. 1.2 mm); Color — green 143C.

Sepals: Quantity — 5; Coloration — green 143C; Shape — conical pointed.

Leaves: Shape — oblanceolate; Length (petiole not included) — medium-long (avg. 89 mm); Width — narrow-medium (avg. 57 mm); Length/width ratio — medium (1.56); Blade margin — crenate; Apex — acuminate; Base shape — oblique; Color of upper surface — green 143A (in early summer); Color of lower surface — green 143C (in early summer); Attitude in relation to shoot — outward.

Petiole: Length — medium (avg. 25 mm); Diameter — medium-thick (avg. 1.4 mm); Coloration — yellow green 145B.

Fruit: Quantity per cluster — 2 to 4; Size — medium (avg. 77 mm); Weight — medium (avg. 200 g); Ratio of height to width — small-medium (0.9); General shape in profile — broad globose to conical/globose to conical; Position of maximum diameter — in middle; Ribbing — absent or very weak; Crowning at calyx end — weak; Size of eye — medium (avg. 9.3 mm); Aperture of eye — fully open; Length of sepal — medium (avg. 5.9 mm); Bloom of skin — absent or very weak; Greasiness of skin — absent or very weak; Background color of skin — yellow 11A; Amount of over color — high; Over color of skin — orange red 34A to red purple 59A: Intensity of over color — medium-dark; Pattern of over color — solid flush with stripes; Lenticels — small, round, white N155D; Amount of russet around stalk cavity —high; Amount of russett on cheeks — absent or very weak; Area of russet around eye basin — absent or very weak; Length of stalk — medium (avg. 18 mm); Thickness of stalk — medium (avg. 2.3 mm); Depth of stalk cavity — medium (avg. 16.5 mm); Width of stalk cavity — medium (avg. 34.5 mm); Depth of eye basin — medium (avg. 7.3 mm); Width of eye basin — medium (avg. 29 mm); Firmness of flesh (measurement with penetrometer) — firm (avg. 7.2); Flesh texture — firm and crunchy; Aroma — aromatic and slightly acidic; Juiciness — medium to high; Brix — 13° brix minimum at harvest time; Flesh coloration — yellow 4C; Stem coloration — yellow green 144B to green brown 199C.

Seeds: Quantity per fruit — 4 on average; Shape — truncate ovoid; Coloration — greyed purple N186C.

Harvest: Time for harvest — medium, second week of September (one week before 'Golden Delicious'); Harvest window — 3 weeks; Number of picks — one to two picks; Amount of fruit produced per tree per harvest — 60 fruits on sixth leaf trees.

Disease resistance: Relatively susceptible to mildew; Average susceptibility to scab; Susceptibility to fire blight is similar to 'Gala.'

I claim:

1. A new and distinct apple tree substantially as described and illustrated herein.

* * * * *